(12) United States Patent
Millard

(10) Patent No.: US 9,011,932 B2
(45) Date of Patent: *Apr. 21, 2015

(54) CONTACT LENS CARE SYSTEM WITH PEROXIDE

(75) Inventor: Kimberly A. Millard, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 894 days.

This patent is subject to a terminal disclaimer.

(21) Appl. No.: 13/189,046

(22) Filed: Jul. 22, 2011

(65) Prior Publication Data

US 2012/0070349 A1    Mar. 22, 2012

Related U.S. Application Data

(60) Provisional application No. 61/383,433, filed on Sep. 16, 2010.

(51) Int. Cl.
*A01N 33/04* (2006.01)
*A01N 59/00* (2006.01)
*A61L 12/12* (2006.01)

(52) U.S. Cl.
CPC ............... *A61L 12/128* (2013.01); *A01N 59/00* (2013.01)

(58) Field of Classification Search
CPC ............. A01N 59/00; A01N 2300/00; A61K 2300/00; A61K 33/40; A61K 31/13; A61K 9/0048
See application file for complete search history.

(56) References Cited

U.S. PATENT DOCUMENTS

| | | | |
|---|---|---|---|
| 3,912,451 A * | 10/1975 | Gaglia, Jr. | 422/30 |
| 4,588,586 A | 5/1986 | Kessler et al. | |
| 4,812,173 A | 3/1989 | Tsao et al. | |
| 4,889,689 A | 12/1989 | Tsao | |
| 5,089,240 A | 2/1992 | Perlaky | |
| 5,196,174 A * | 3/1993 | Cerola et al. | 422/300 |
| 5,209,865 A | 5/1993 | Winterton et al. | |
| 5,270,002 A | 12/1993 | Neff, II et al. | |
| 5,306,352 A | 4/1994 | Nicolson et al. | |
| 5,422,073 A * | 6/1995 | Mowrey-McKee et al. | 422/28 |
| 5,523,012 A | 6/1996 | Winterton et al. | |
| 5,756,045 A | 5/1998 | Mowrey-McKee et al. | |
| 5,869,532 A | 2/1999 | Mizushima et al. | |
| 7,022,654 B2 | 4/2006 | Tsao | |
| 2008/0185298 A1 | 8/2008 | Kanner et al. | |
| 2011/0114517 A1 | 5/2011 | Minick et al. | |

FOREIGN PATENT DOCUMENTS

| | | |
|---|---|---|
| EP | 0265381 A2 | 4/1988 |
| JP | 1152309 | 2/1999 |
| WO | WO 9603157 A1 | 8/1996 |
| WO | WO 02/26922 | 4/2002 |
| WO | WO 2008/077106 A1 | 6/2008 |

* cited by examiner

*Primary Examiner* — Abigail Fischer
*Assistant Examiner* — Jessica Kassa
(74) *Attorney, Agent, or Firm* — Toan P. Vo

(57) ABSTRACT

A contact lens disinfection system that includes a peroxide disinfection solution in combination with a lens closure. The disinfection solution comprises 0.5 wt. % to 6 wt. % hydrogen peroxide or a chemical precursor of hydrogen peroxide, and an amino buffer component. The closure includes securing elements to position and maintain a pair of contact lenses in the disinfection solution, and a peroxide neutralization catalyst comprising platinum. In combination with the closure, the disinfection solution exhibits a pseudo first-order, half-life of hydrogen peroxide over an initial sixty minutes of neutralization from 12 minutes to 30 minutes in the lens closure.

14 Claims, 7 Drawing Sheets

CONTACT LENS CARE SYSTEM WITH PEROXIDE

CROSS REFERENCE

This application claims the benefit of copending U.S. application Ser. No. 13/012,018 filed Jan. 24, 2011 and Provisional Patent Application No. 61/383,433 filed Sep. 16, 2010, the disclosures of which are incorporated by reference herein.

FIELD OF THE INVENTION

The invention relates to a contact lens care system that utilizes hydrogen peroxide and methods for cleaning and disinfecting contact lenses, particularly, soft hydrogel contact lenses.

BACKGROUND OF THE INVENTION

Disinfection solutions for the care of contact lenses are well known in the art and the use of such lenses and solutions often involves a daily disinfection regimen. The present market of lens care solutions includes multipurpose solutions, which include one or more antimicrobial components, and solutions that include about 3 wt. % hydrogen peroxide. Potentially, one advantage of a hydrogen peroxide lens care disinfection system is the absence of a disinfection agent in the solution or the lens following neutralization of the hydrogen peroxide with the exception of residual amounts of hydrogen peroxide, generally less than 100 ppm.

In general, hydrogen peroxide disinfection systems include a hydrogen peroxide disinfection solution and a contact lens closure into which the contact lenses to be disinfected are placed in retaining basket-like structures. Once retained the lenses are placed in contact with the disinfection solution for a required period of time. Following or simultaneous with this disinfection cycle the peroxide solution requires neutralization, and this can be carried out either by catalytic reduction with a supported platinum catalyst or with an enzyme such as catalase. Following neutralization the contact lenses are removed from the closure and can be reinserted onto the eye without a separate rinse step as the hydrogen peroxide has been neutralized to levels that are non-irritating to ocular tissues.

Consumer friendly, single step peroxide disinfection systems have obtained almost exclusive popularity, e.g., the AO Sept system by CibaVision and the EZ Sept system by Bausch+Lomb. These two systems operate by placing a contact lens to be disinfected in contact with a solution of peroxide and a platinum disk whereby peroxide disinfection of the lens and neutralization of the peroxide occur simultaneously. The user places the lenses in the lens holding compartments, adds the disinfection solution to the system container, closes the container placing the lenses in contact with the solution and waits the appropriate time interval, typically four to eight hours, before removing the lenses from the disinfection system. The lenses can then be directly inserted onto the eye.

In hydrogen peroxide systems that rely upon a platinum catalyst for neutralization the hydrogen peroxide is depleted very rapidly. Consequently, lens disinfection at the higher peroxide concentrations is somewhat limited in time. For example, in an AO Sept system in which the initial concentration of hydrogen peroxide is 3%, the concentration of the hydrogen peroxide falls rapidly to about 0.1% in about 12.5 minutes. See, U.S. Pat. No. 5,306,352. After this point, the neutralization of the remaining hydrogen peroxide proceeds relatively slowly and it takes several hours, i.e. up to 8 hours or more, before the hydrogen peroxide is depleted sufficiently so that the contact lens can be inserted onto the eye without fear of irritation or injury.

U.S. Pat. No. 5,306,352 to Nicolson et al. recognizes the need to control the catalytic decomposition or neutralization reaction of the hydrogen peroxide such that concentration of the hydrogen peroxide remains at higher levels during the initial stages of neutralization, yet maintain the necessary degree of neutralization to allow for direct insertion of the disinfected lens onto the eye without the need for rinsing the lenses. In FIG. 1 the hydrogen peroxide neutralization rate of the AO Sept system is plotted in which a platinum catalyst is contacted with a 3% hydrogen peroxide solution. In such situation, it is noted that the concentration of the hydrogen peroxide falls rapidly to about 0.1% in about 12 minutes. FIG. 2 represents a decomposition profile of a hydrogen peroxide system in which the rate of decomposition of the hydrogen peroxide is said to be controlled by means described by Nicolson.

Nicolson generally describes five steps to consider in the catalytic decomposition of hydrogen peroxide: (1) the transportation of the hydrogen peroxide to the catalyst to insure a continuous contact between the catalyst and hydrogen peroxide; (2) the absorption of hydrogen peroxide to the catalyst surface; (3) the neutralization or catalysis in which the hydrogen peroxide is decomposed to water and nascent oxygen; (4) the desorption from the surface of the reaction products, i.e. the water and nascent oxygen, or other contaminants so as to expose the active sites; and (5) the transportation of the reaction products away from the catalytic surface. Unfortunately, Nicolson does not clearly describe how one of skill might actually control any one of these reaction (neutralization) stages to achieve a desired neutralization curve.

With respect to step (3), Nicolson proposes that the catalyst be partially poisoned in the manufacturing setting prior to sale and first use by the consumer. To determine whether the catalyst is sufficiently pre-poisoned, the generation of oxygen from the system can be measured. As stated, in a typical AO Sept system using platinum as a catalyst one can estimate the rate of neutralization from the initial generation of oxygen at about 40 mL/min. Nicolson proposes that the catalyst be sufficiently pre-poisoned so that the amount of oxygen liberated during the reaction is periodically measured until the oxygen liberation rate is somewhere between 2 and 15 mL/min, and preferably between 2 and 5 mL/min. Again, there is no description in Nicolson as to how one might pre-poison a platinum catalyst to achieve the proposed peroxide neutralization rate.

Instead, Nicolson focuses on a mechanical/chemical means referred to as a "buoyance mediated control system" to delay hydrogen peroxide neutralization in contact lens disinfection systems. It is stated that the absorption of generated oxygen gas provides a neutralizing catalytic particle with sufficient buoyancy to rise to the surface of the peroxide solution. Buoyancy controlled catalytic reactions fall into two primary types of reactions. First are those reactions which generate a gas. The gas bubbles adhere to the surface of the catalyst particle creating a buoyant particle. The buoyant particle rises to the surface where the gas bubble escapes to the gas phase over the liquid reaction medium. Upon losing the gas bubbles, the catalyst loses buoyance and begins to descent until it again contacts liquid containing reactants so that further buoyant gas bubbles can be generated. This bobbing action is, therefore, confined to the uppermost layers of the solution leaving the lower portion of the solution in a relatively non-neutralized state for a greater period of time.

In the second type of buoyancy controlled catalytic reaction, the catalytic particle resides at or near top of the solution due to its density. If the reaction product solution is less dense than the reactant solution, then the reaction proceeds substantially from top to bottom and the catalytic particles are designed to be slightly less dense than the reactant solution (i.e. between the reaction product and reactant solution densities). If the reaction product solution is more dense than the reactant solution, then the reaction proceeds from bottom to top and the catalytic particle is designed to be slightly more dense than the reactant solution. In either event, the catalytic particle must return to contact the reactant solution if the neutralization reaction is to proceed. In either case, these buoyancy controlled processes are very complex and impose substantial limitations on commercial applications.

The presently marketed, one-step peroxide disinfection systems have been around for over twenty-five years with little or no improvement in disinfection profile against selected U.S. FDA bacteria/fungal microorganisms. Surfactants have been added to assist in protein and lipid cleaning, but little, if any, progress has been made to improve upon the biocidal effectiveness of lens care peroxide disinfection systems. Neither have there been any advances in peroxide disinfection systems that makes it possible to control the neutralization rate of the hydrogen peroxide. There is a need to address these drawbacks in the currently marketed lens care peroxide systems, and to improve upon the disinfection and effective storage of the lenses following complete neutralization of the hydrogen peroxide.

SUMMARY OF THE INVENTION

A contact lens disinfection system comprising a peroxide disinfection solution in combination with a lens closure. The disinfection solution comprises 0.5 wt. % to 6 wt. % hydrogen peroxide or a chemical precursor of hydrogen peroxide, and an amino buffer component. The lens closure comprises securing elements to position and maintain a pair of contact lenses in the disinfection solution, and a peroxide neutralization catalyst comprising platinum. In combination with the lens closure, the disinfection solution exhibits a pseudo first-order, half-life of hydrogen peroxide over an initial sixty minutes of neutralization from 12 minutes to 30 minutes in the lens closure.

In another embodiment, the disinfection solution in combination with the lens closure will exhibit greater biocidal efficacy against *Candida albicans* or *Serratia marcescens* by 0.5 log-kill or greater after six hours than an equivalent contact lens disinfection solution in the absence of the amino buffer component. The increase in effectivness against *Candida albicans* or *Serratia marcescens* is provided by a delay in peroxide neutralization of the solution.

A contact lens disinfection system comprising a peroxide disinfection solution in combination with a lens closure. The disinfection solution comprises 0.5 wt. % to 6 wt. % hydrogen peroxide or a chemical precursor of hydrogen peroxide, and an amino buffer component selected from the group consisting of 2-amino-2-hydroxymethyl-1,3-propane diol, 2-[Bis(2-hydroxyethyl)amino]-2-(hydroxymethyl)-1,3-propanediol, and N-(2-acetoamido)-2-aminoethanesulfonic acid. Again, in combination with the lens closure, the disinfection solution exhibits a pseudo first-order, half-life of hydrogen peroxide over an initial sixty minutes of neutralization from 12 minutes to 30 minutes in the lens closure.

BRIEF DESCRIPTION OF THE DRAWINGS

The invention will be better understood from the following description and in consideration with the accompanying Figures. It is to be understood, however, that each of the Figures is provided to further illustrate and describe the invention and is not intended to further limit the invention claimed.

DETAILED DESCRIPTION OF THE INVENTION

Figure 1:
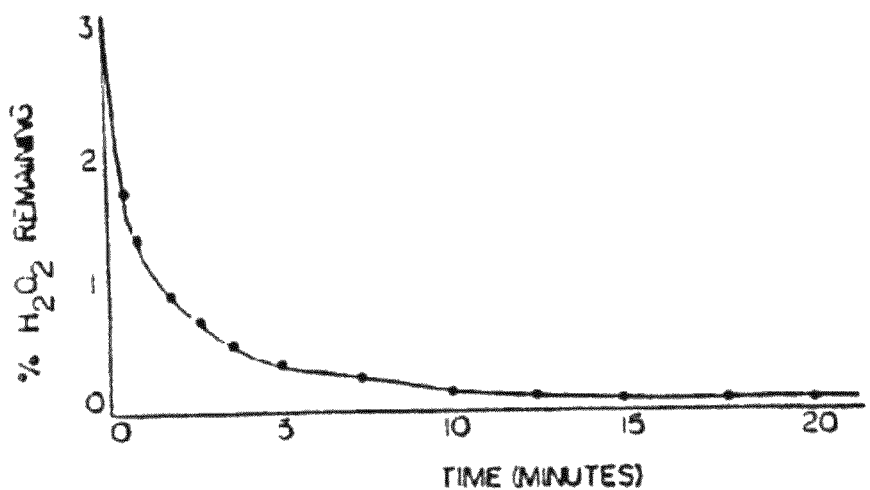
FIG. 1 is a neutralization rate profile of a contact lens peroxide disinfection solution of the prior art.
Figure 2:
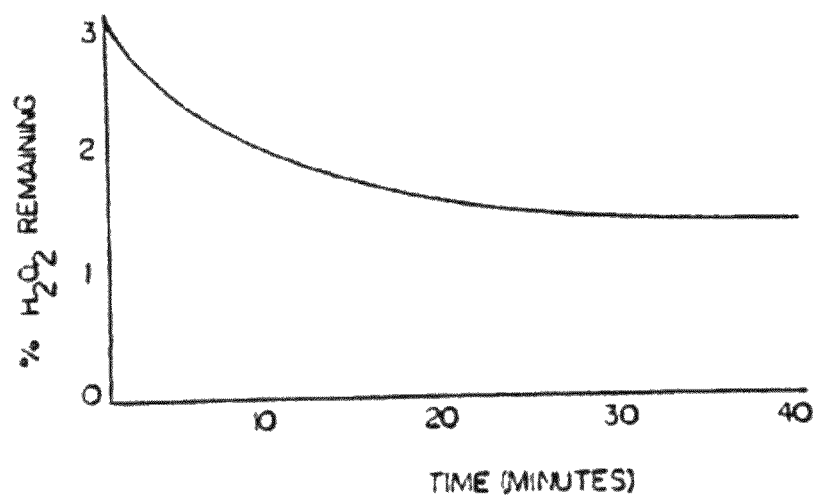
FIG. 2 is a neutralization rate profile of a proposed contact lens peroxide disinfection system of the prior art.
Figure 3:
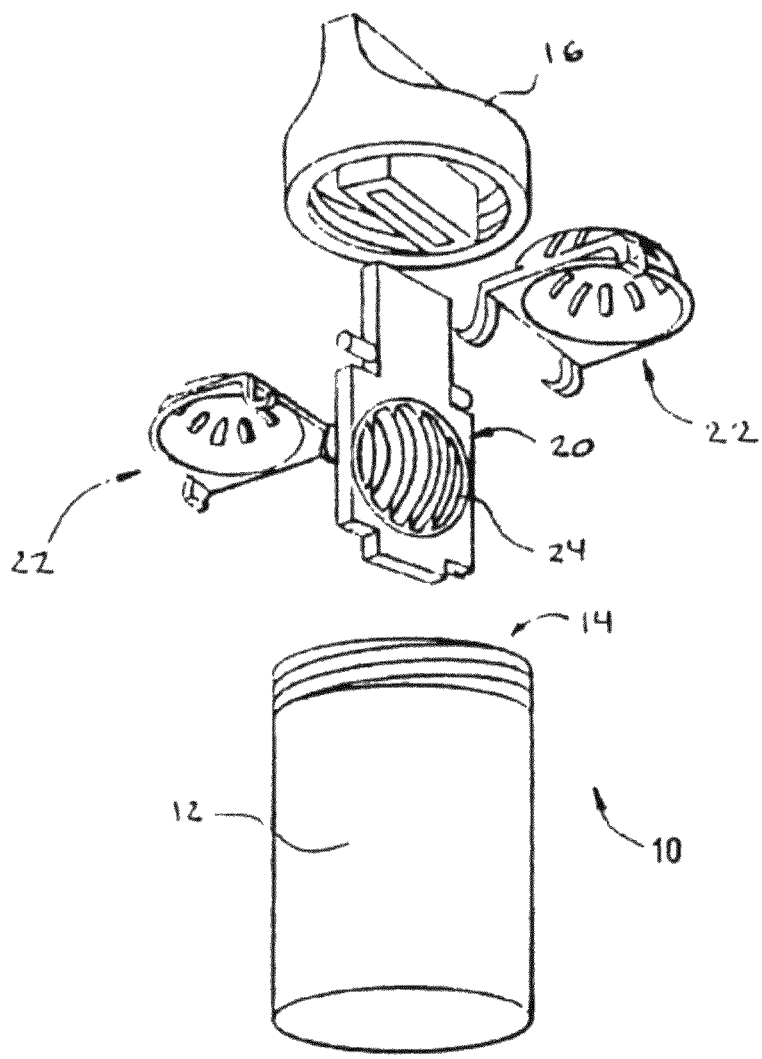
FIGS. 3 and 4 are prior art lens case closures for cleaning and disinfection contact lenses using a peroxide disinfection solution.

Contact lens disinfection closures designed for use with peroxide-based, contact lens disinfection solutions are well known. U.S. Pat. No. 5,196,174 to Cerola et al. and U.S. Patent Pub. No. 20080185298 to Kanner et al. describe such systems, the entire disclosures of which are incorporated herein by reference. One embodiment of a contact lens closure is shown in FIG. 3. The contact lens disinfection closure apparatus 10 includes a container or reaction vessel 12, and terminates in an open top 14 which preferably has a thread for engaging a complementary thread formed within a cap member 16. This reaction vessel or container 12 is particularly adapted to contain a quantity of an aqueous hydrogen peroxide disinfection solution. In accordance with prevailing practice, the hydrogen peroxide is of a relatively low concentration, and preferably no more than a 6 wt. % solution of hydrogen peroxide. The cap member 16 includes securing elements to position and maintain a pair of contact lenses in the disinfection solution. As shown, the securing elements include a lens supporting assembly 20 that comprises a pair of basket-type lens support structures 22. Each lens supporting assembly comprises a base that includes a lens-supporting dome or semi-spherical portion 24 complementary to the lens support structures 22.

Figure 4:
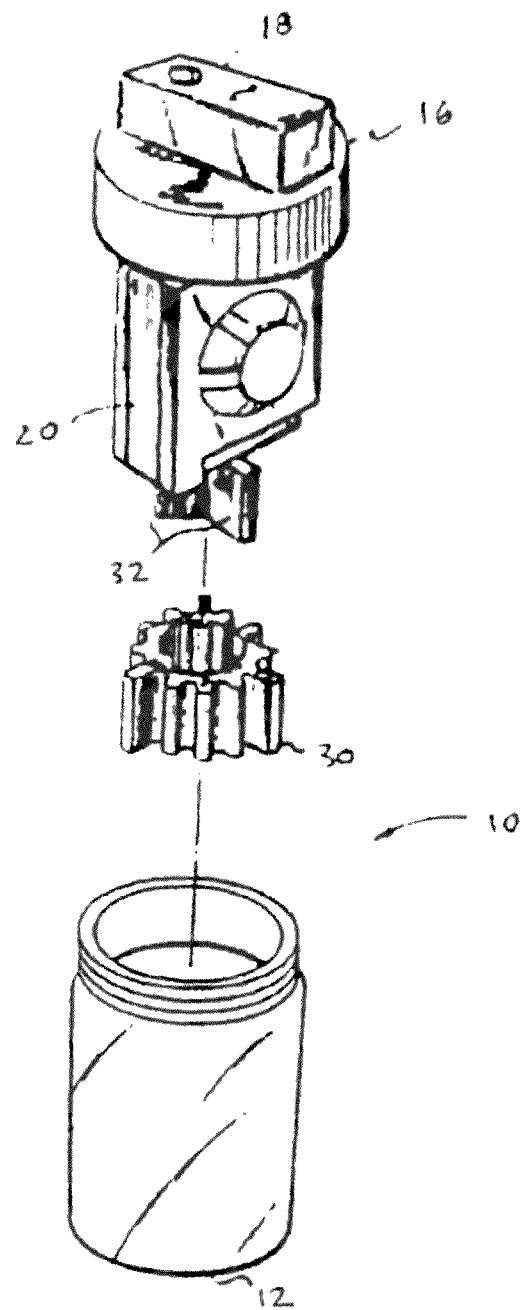

As shown in FIG. 4, the contact lens closure apparatus 10 also includes a catalytic element 30 such as a platinum-coated substrate that catalyzes the decomposition of the hydrogen peroxide in the disinfection solution to dioxygen and water. The catalytic element 30 can be attached to a connecting member 32 proximate to an end of the lens supporting assembly 20 opposite from cap member 16. Preferably, the peroxide decomposition or neutralization process is arranged to occur over a period of several hours, e.g., from 2 to 6 hours, depending on the nature of the catalytic element and the initial concentration of the hydrogen peroxide in the disinfection solution. Generally, it is recommended that the consumer conduct the neutralization process overnight in order to assure near-complete decomposition of the hydrogen peroxide. Cap member 16 also includes a gas venting member 18 which enables the dioxygen produced during the peroxide neutralization reaction to escape a closed lens closure.

The present invention is directed to a contact lens disinfection system that includes a disinfection solution in combination with a lens closure. The solution comprises 0.5 wt. % to 6 wt. % hydrogen peroxide or a chemical precursor of hydrogen peroxide, and an amino buffer component. The lens closure comprises securing elements to position and maintain a pair of contact lenses in the disinfection solution, and a peroxide neutralization catalyst comprising platinum. In combination with the closure, the disinfection solution exhibits greater biocidal efficacy against *Candida albicans* or *Serratia marcescens* by 0.5 log-kill or greater after six hours than an equivalent contact lens disinfection solution in the absence of the amino buffer component. The increase in effectivness against *Candida albicans* or *Serratia marcescens* is provided by a delay in peroxide neutralization of the solution, particularly, during the first few minutes to 30 or 60 minutes following contact of the solution with the catalyst.

The presence of the amino buffer component in the disinfection hydrogen peroxide solution slows the rate at which the hydrogen peroxide is neutralized, particularly during the first two hours, by a catalyst element that contains platinum. This reduction in rate of peroxide neutralization provides a more effective solution for killing certain microorganisms and fungi. The disinfection peroxide systems are effective against a wide spectrum of microorganisms, including but not limited to *Staphylococcus aureus, Pseudomonas aeruginosa, Serratia marcescens, Candida albicans*, and *Fusarium solani*. The peroxide disinfection systems are particularly effective against *Candida albicans* or *Serratia marcescens* as evidenced by 0.5 log-kill or greater than an equivalent contact lens disinfection solution in the absence of the amino buffer component.

Aside from the FDA-specified representative bacteria and fungi, Acanthamoeba is another organism that is resistant to most antimicrobial agents. A recent increase in Acanthamoeba infection among contact lens wearers in the U.S. indicates a need for a contact lens disinfection system that exhibits a greater biocidal effect on Acanthamoeba. The disinfection lens care system of the invention exhibits superior biocidal efficacy against the FDA-bacteria/fungi above, and equal or better biocidal efficacy against Acanthamoeba, than the current Clear Care® disinfection system on the market. Again, it is the delay in the neutralization of the hydrogen peroxide over the initial 60 minutes of disinfection time that is believed to provide the superior biocidal results.

The overall antimicrobial effect for a tested peroxide disinfection system is determined by adding $1 \times 10^5$ to $1 \times 10^6$ microbes into a given hydrogen peroxide lens case filled with 10 mL of a test solution. The lens closure is closed with a cap to which is attached a cap stem with a catalytic disk immediately after the introduction of the microbes. Kill is measured by log reduction at 4 or 6 hours and 24 hours. See Example section for more experimental details on determining the biocidal effectiveness for the described peroxide lens care systems.

The term "hydrogen peroxide" includes a stabilized form of hydrogen peroxide. Exemplary stabilized forms of hydrogen peroxide are described in U.S. Pat. Nos. 4,812,173 and 4,889,689, the entire disclosures of which are incorporated herein by reference. The term "a chemical precursor of hydrogen peroxide" is a chemical compound that dissociates in water to form an aqueous hydrogen peroxide solution, wherein the amount of discociative hydrogen peroxide following complete dissociation is from 0.05 wt. % to 6 wt. %. Exemplary chemical precursors of hydrogen peroxide include sodium perborate, sodium percarbonate, urea hydrogen peroxide and sodium perpyrophosphate. It is of course understood by those of skill in the art that the described peroxide lens care solutions can include both a stabilized form of hydrogen peroxide and a chemical precursor of hydrogen peroxide, however, the total concentration of hydrogen peroxide does not exceed 6 wt. %

In one embodiment, the amino buffer component can be any buffer component with a primary, secondary or tertiary amino group and two (2) to sixteen (16) carbon atoms. The amino buffer component can also include one or more hydroxyl functional groups, and preferably, two or more hydroxyl functional groups. One example of an amino buffer component with a tertiary amino functionality and eight (8) carbons is 2-[Bis(2-hydroxyethyl)amino]-2-(hydroxymethyl)-1,3-propanediol, or what is commonly referred to as Bis-TRIS.

In another embodiment, the amino buffer component is a buffer component with a primary or secondary amino group and two (2) to twelve (12) carbon atoms. The amino buffer component can also include one or more hydroxyl functional groups, and preferably, two or more hydroxyl functional groups. One example of an amino buffer component with a primary amino functionality and four (4) carbons is 2-amino-2-hydroxymethyl-1,3-propane diol, or what is commonly referred to as TRIS. One example of an amino buffer component with a secondary amino functionality and four (4) carbons is N-(2-acetoamido)-2-aminoethanesulfonic acid, or what is at times referred to as N-(Carbamoylmethyl)taurine.

In one embodiment, the amino buffer component is 2-amino-2-hydroxymethyl-1,3-propane diol (TRIS). In many preferred embodiments, TRIS is present at a concentration from 0.01 wt. % to 0.6 wt. %, or from 0.08 wt. % to 0.3 wt. %.

In another embodiment, the amino buffer component is 2-[Bis(2-hydroxyethyl)amino]-2-(hydroxymethyl)-1,3-propanediol (Bis-TRIS). The bis-TRIS is present at a concentration from 0.01 wt. % to 0.6 wt. %, or from 0.08 wt. % to 0.3 wt. %.

In another embodiment, the amino buffer component is N-(2-acetoamido)-2-aminoethanesulfonic acid, which is present at a concentration from 0.01 wt. % to 0.6 wt. %, or from 0.08 wt. % to 0.3 wt. %.

In other embodiments, the amino buffer component is an amino acid or a compound derived from an amino acid. Exemplary amino acids are selected from the group consisting of methionine, aspargine, glutamine, histidine, lysine, arginine, glycine, serine, cystine and threonine. Cystine is an oxidized, disulfide form of cysteine. In many preferred embodiments, the amino acid-based buffer component is present in the described peroxide solutions at a concentration from 0.01 wt. % to 2.0 wt. %, from 0.05 wt. % to 0.6 wt. %, or from 0.08 wt. % to 0.4 wt. %.

The peroxide disinfection solution of the disinfection system can include other components to complement the amino buffer component. Typically, the amino buffer component will require a complementary conjugate acid to provide greater buffer capacity for the peroxide solutions. The buffer system present in the solutions maintains the pH in a physiologically acceptable range of about 5 to about 8. One example of a conjugate acid buffer component is citric acid. Another buffer system includes TRIS with an amino acid such as glycine, aspartic acid or glycolic acid.

As stated, the hydrogen peroxide is present at a concentration that is suitable for disinfecting a contact lens including soft and RGP lenses, and in particular, a silicone hydrogel contact lens, against a wide spectrum of microorganisms, including but not limited to *Staphylococcus aureus, Pseudomonas aeruginosa, Serratia marcescens, Candida albicans,* and *Fusarium solani*. The hydrogen peroxide is present from 0.5 wt. % to about 6 wt. %, from 2 wt. % to 4 wt. %, or about 3 wt. % such as 3.0 wt. % to 3.5 wt. %. The amount of hydrogen peroxide in the solution is dependent upon a number of parameters including the type and concentration of the amino-buffer component present in the solution.

In many instances, the appropriate peroxide concentration is determined by the time it takes to neutralize the hydrogen peroxide to an ophthalmically safe level for a given catalytic element and for a given solution. Ideally, the residual peroxide content should be within an ophthalmically safe level preferably within less than about 8 hours, preferably less than about 6 hours, more preferably less than about 4 hours. By the term "ophthalmically safe" with respect to a contact-lens solution is meant that a contact lens treated with the solution is safe for direct placement on the eye without rinsing, that is, the solution is safe and sufficiently comfortable for daily contact with the eye via a contact lens. Although most patients can tolerate about 200 ppm of residual peroxide in a contact lens disinfection solution, the target level of peroxide at or near complete neutralization is less than about 130 ppm or less than about 100 ppm.

The molar ratio of hydrogen peroxide to the amino buffer component in the described peroxide lens care solutions can be important because the molar ratio appears to have some affect on the neutralization profile of the hydrogen peroxide with the neutralization catalyst. As stated, the superior biocidal performance of the described contact lens, peroxide disinfection systems is believed to result from slowing the rate of peroxide neutralization over the first one or two hours following contact of the peroxide solution with the neutralization catalyst. It is proposed that the amino buffer component competes with the hydrogen peroxide for the active catalytic sites of the neutralization catalyst. It is also proposed that the amino buffer component can modulate the relatively more active neutralization sites on the catalyst surface. One of skilled in the art would expect that this competition for the active catalytic sites of the catalyst is concentration dependent.

In many embodiments, the molar ratio of hydrogen peroxide to the amino buffer component in the disinfection solution is from 10:1 to 200:1 or from 10:1 to 100:1.

Comparative Ex. No. 1. Clear Care® lens care peroxide solution manufactured by CibaVision, Inc. Using the assay method described herein we have determined the hydrogen peroxide concentration in Clear Care® to be from 3.3 wt. % to 3.5 wt. %.

Comparative Ex. No. 2. In accordance with U.S. Pat. No. 7,022,654, Applicants also prepared peroxide lens care solutions containing: 0.077 wt. % sodium phosphate; 0.156 wt. % disodium phosphate; 0.79 wt. % NaCl; 0.05 wt. % Pluronic® 17R4 and 3.0 wt. % stabilized hydrogen peroxide. Applicants believe that this comparative example formulation is representative of the solution components and their respective concentration for Clear Care®.

EXAMPLE 1

A peroxide disinfection solution is prepared in reference to Comparative Ex. 2 with the exception that citric acid 0.15 wt. % and TRIS 0.12 wt. % are substituted for the sodium phosphate and disodium phosphate. In other words, the phosphate buffer system has been replaced by the citric acid/TRIS buffer system.

Figure 5A:
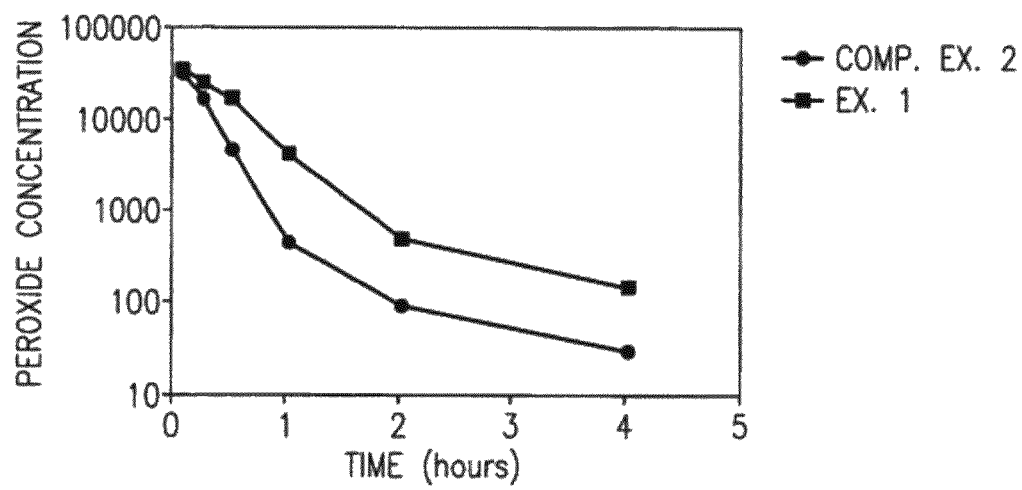
FIG. 5A is a comparative plot of neutralization rate profiles of a peroxide disinfection solution of the invention against a similar peroxide solution but with a phosphate buffer.
Figure 5B:
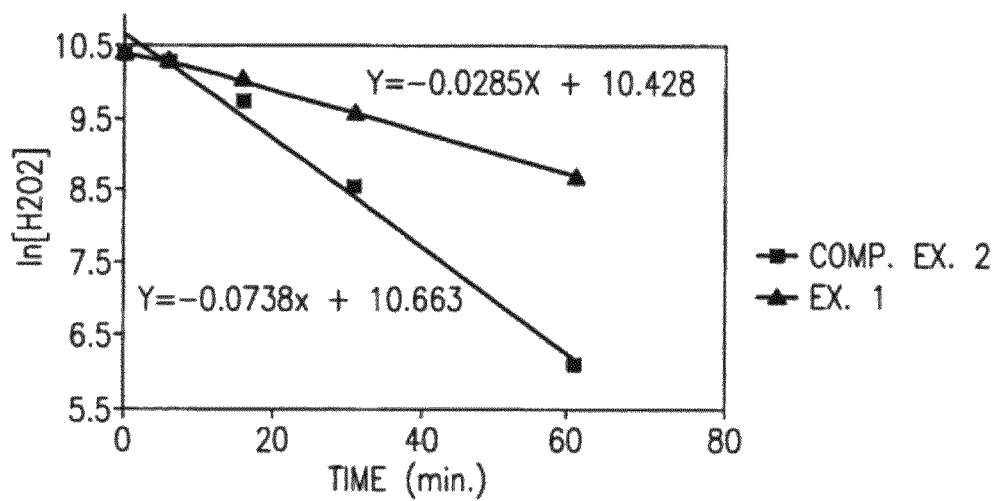
FIG. 5B is a graphical representation for determining the pseudo first-order rate constants for the neutralization of hydrogen peroxide disinfection solutions of FIG. 5.

FIG. 5A is a peroxide neutralization plot for two solutions: Comparative Ex. No. 2 and Example No. 1. Example 1 was formulated to model a commercial Clear Care® solution except for the substitution of TRIS buffer for the phosphate buffer. As indicated by the plot data, a significant reduction in the rate of peroxide neutralization over the initial two hours is observed with a peroxide disinfection solution with an amino buffer component, TRIS, in comparison to a Clear Care®-like solution with a phosphate buffer system (other solution components and their respective concentrations being the same). The line plots shown in FIG. 5B are determined from the peroxide neutralization data of the solutions of FIG. 5A over the initial 60 minutes, i.e. at time of 0, 5 min, 15 min, 30 min and 60 min. The pseudo first-order rate constants are tabulated below along with the corresponding half-life ($\tau_{1/2}$) values.

| Solution | k (min$^{-1}$) | $\tau_{1/2}$ (min) |
| --- | --- | --- |
| Comp. Ex. 2 | 0.076 | 9.4 |
| Example 1 | 0.029 | 24 |

Accordingly, one embodiment of the contact lens disinfection system comprises a peroxide disinfection solution that includes 0.5 wt. % to 6 wt. % hydrogen peroxide or a chemical precursor of hydrogen peroxide, and an amino buffer component, and a lens closure. The lens closure comprises securing elements to position and maintain a pair of contact lenses in the disinfection solution, and a peroxide neutralization catalyst comprising platinum. The disinfection system will exhibit a pseudo first-order, half-life of hydrogen peroxide over an initial sixty minutes of neutralization from 12 minutes to 30 minutes, as measured in a given hydrogen peroxide, contact lens disinfection closure equipped with a catalyst comprising platinum. Exemplary peroxide disinfection systems will have a pseudo first-order, half-life of hydrogen peroxide over the initial sixty minutes of neutralization from 14 minutes to 22 minutes. It is preferred that the concentration of hydrogen peroxide after an initial six hours of neutralization is less than 150 ppm, preferably less than 120 ppm, more preferably less than 100 ppm.

The peroxide neutralization rate profiles of select disinfection solutions were determined as follows. Each solution (10 mL) was placed in a peroxide contact lens closure supplied with a marketed Clear Care® peroxide system. The top cap portion equipped with a platinum element is then screwed to the container thereby submerging the platinum element into the solution. Immediate peroxide neutralization is observed with the evolution of gas. Aliquots of the solution are removed at the stated time points and the concentration of hydrogen peroxide is determined by known analytical methods.

The aliquots of solution are titrated with 0.1N potassium permanganate in the presence of an acidic aqueous solution. To perform this titration, a Mettler Toledo Titration Excellence T50 System (Mettler Toledo, Columbus, Ohio) is used. A 3.0 mL aliquot of sample is added to 60 mL of water and 1.25 mL of 20% sulfuric acid solution. The sample is placed in the system and analyzed using a built-in hydrogen peroxide determination method. A Mettler Toledo Plug & Play DMi140-SC Platinum Ring Electrode (Mettler Toledo, Columbus, Ohio) is used to determine the electrochemical equivalence endpoint of the titration. Once an endpoint is determined the instrument calculates the hydrogen peroxide concentration of the sample. The determined peroxide concentrations are used to provide the peroxide neutralization plots.

Of course, contact lens disinfection solutions containing hydrogen peroxide, or a chemical precursor of hydrogen peroxide, will also include other solution components including one or more surfactants to assist in the removal of denatured tear proteins and environmental containments, and one or more tonicity agents to adjust the osmolality of the solution. The contact lens solution can also include one or more comfort or wetting components to provide lubrication or a moisturizing affect to a disinfected contact lens.

Suitable surfactants can be generally described as block copolymers of a hydrophile and hydrophobe terminated in either primary or secondary hydroxyl groups. A first example of such surfactants are polyoxyethylene/polyoxypropylene condensation polymers. Such block copolymers can be obtained commercially from the BASF Corporation under the trademark Pluronic®. Low foaming surfactants are particularly applicable in peroxide-based solutions. A particular polyoxyethylene/polyoxypropylene condensation polymer is prepared by first synthesizing a polyoxyethylene chain of desired molecular weight by the controlled addition of ethylene oxide to ethylene glycol. In the second step of the synthesis, propylene oxide is added to create hydrophobic blocks on the outside of the molecule. Such block copolymers can be obtained commercially from the BASF Corporation under the trademark Pluronic® R, and are generally known in the art as low foam surfactants. The letter R found in the middle of the designation of the Plutonic® series signifies that this product has a reverse structure compared to the Plutonic® products, i.e., the hydrophile (ethylene oxide) is sandwiched between the propylene oxide blocks.

The concentration of a surfactant component in the lens care peroxide solution varies over a wide range depending on a number of factors, for example, the specific surfactant or surfactants being used, and the other components in the solution. Often the amount of surfactant is in the range of 0.005 wt. % to 0.8 wt. %, or from 0.01 wt. % to 0.5 wt. %. Preferably, the surfactant is present in an amount less than 0.2 wt. %; and most preferably less than 0.1 wt. %.

The sequence and percent distribution of hydrophobic and hydrophilic segments in these block copolymers leads to important differences in surfactant properties. The surfactant is preferably a liquid at 20 ° C. The molecular weight of the polyoxypropylene block is preferably from 1000 to 2500. Most preferably, the molecular weight of the polyoxypropylene block is approximately 1700. Specific examples of Pluronic® surfactants that are satisfactory include: Pluronic® L42, Pluronic® L43, Plutonic® L61 and Plutonic® L81. Specific examples of Plutonic® R surfactants that are satisfactory include: Plutonic® 31R1, Plutonic® 31R2, Plutonic® 25R1, Plutonic® 17R1, Pluronic® 17R2, Pluronic® 12R3. Particularly good results are obtained with Pluronic® 17R4 surfactant and Pluronic® L81.

When selecting the structure of a block copolymer surfactant, it is preferred to select a surfactant that limits the amount of foaming of the solution because many surfactants will cause excessive foaming as oxygen is generated by the decomposition of the hydrogen peroxide upon contact with the catalytic disk. Block copolymers with low ethylene oxide content are the most effective defoamers. Within each series of block copolymer products, defoaming performance increases as ethylene oxide content decreases and molecular weight increases. The tendency of a surfactant to create and/or sustain foam is measured according to the Ross-Miles test protocol ASTM designation D-1173-53 (0.1%, at 50 ° C.). Moreover, one of ordinary skill in the art could easily identify, and therefore select, low foam Pluronic®-type surfactants merely by reviewing the Tables of surfactant properties in a product brochure, Surfactants, Pluronics & Tetronics, BASF Corporation 1999, pp. 24-31.

The composition of the present invention preferably contains a hydrogen peroxide stabilizer. Preferably, the stabilizer is a diphosphonic acid alkanol as disclosed in U.S. Pat. No. 4,812,173. The most preferred stabilizer is diethylene triamine penta-(methylenephosphonic acid) or a physiologically compatible salt thereof. This compound is manufactured by Solutia under the name DEQUEST®2060. The stabilizer is preferably present in the solution in an amount between about 0.001 and about 0.03% by weight of the composition, and most preferably between about 0.006 and about 0.0120% by weight of the solution. Stabilization of hydrogen peroxide in contact lens disinfection systems is described in more detail in U.S. Pat. Nos. 4,812,173 and 4,889,689. The stabilized form of hydrogen peroxide used in the Example formulations described herein was obtained from Solvay Chemicals, Inc. If desired, additional conventional stabilizers may be employed in conjunction with or in place of the diethylene triamine penta-(methylenephosphonic acid) if it is compatible with the material to be sterilized.

The peroxide disinfection solutions can include an effective amount of a tonicity component to provide the liquid medium with the desired tonicity. Such tonicity components may be present in the solution and/or may be introduced into the solution. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). For example, sodium chloride can be present in the range of 0.50% to 0.90% (w/v).

The described solutions can also include a wetting agent to help maintain the lens in a moistened condition and to help with initial comfort upon placement of the disinfected contact lens upon the eye. Exemplary wetting agents include propylene glycol, glycerin, a sugar alcohol and dexpanthenol. The wetting agents are generally present in the solution at a concentration from 0.2 wt. % to 1.5 wt. %.

Methods for treating a contact lens using the herein described lens care solutions containing peroxide are well known and are included within the scope of the invention. Such methods comprise contacting a contact lens with the described peroxide solutions at conditions effective to provide the desired treatment to the contact lens. In affect, the same procedures that have been used to disinfect and clean contact lenses with a peroxide solution and a peroxide lens closure for the past thirty years can be used with the systems described. The lenses are removed from the eye and placed in the securing elements of the closure. The closure is filled with the disinfection solution and the secured lenses placed in the solution. Contacting at or about ambient temperature and pressure is very convenient and useful. The contacting preferably occurs for a time in the range of about 1 hour to about 12 hours or more. The lenses are then removed from the securing elements and placed on the eye.

The additional non-limiting examples illustrate certain aspects of the present invention.

EXAMPLES 2 to 6

The following peroxide contact lens care solutions were prepared by adding the appropriate amounts of each of the listed components to an aqueous solution that also contains 0.1 wt. % KCl, 0.15 wt. % citric acid, 1.0 wt. % propylene glycol, and poloxamer L81 (60 ppm), see Table 1. The concentrations are listed in wt. % unless noted as ppm. The pH is adjusted to about 6.75 with appropriate amounts of hydrochloric acid or sodium hydroxide.

TABLE 1

| | Example No. | | | | | |
|---|---|---|---|---|---|---|
| | CE3 | CE4 | 2 | 3 | 4 | 5 | CE 5 |
| TRIS base | — | — | 0.12 | 0.12 | 0.12 | 0.12 | — |
| Na phosphate dibasic | 0.55 | 0.55 | — | — | — | — | 0.55 |
| NaCl | 0.1 | — | 0.38 | 0.38 | 0.37 | 0.37 | 0.38 |
| hydrogen peroxide$^a$ | 3.0 | 3.0 | 3.0 | 3.2 | 3.2 | 3.0 | 3.0 |
| taurine (ppm) | 50 | 100 | — | 50 | 100 | 100 | — |

ISO Biocidal Stand-Alone Data

In order to assess the biocidal activity of a particular lens care solution Applicants use the "Stand-Alone Procedure for Disinfection Products" based on the Disinfection Efficacy Testing for Products dated May 1, 1997, prepared by the U.S. Food and Drug Administration, Division of Ophthalmic Devices. This performance requirement does not contain a rub procedure. The stand-alone test challenges a disinfection product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 µm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1 \times 10^7$ to $1 \times 10^8$ cfu/mL. The appropriate cell concentration may be estimated by measuring the turbidity of the suspension, for example, using a spectrophotometer at a preselected wavelength, for example, 490 nm. A peroxide lens disinfection case containing a minimum of 10 mL of test solution per challenge organism is prepared. Each peroxide disinfection case containing the solution to be tested is inoculated with a suspension of the test organism sufficient to provide a final count of $1 \times 10^5$ to $1 \times 10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfulplate for mold except when colonies are observed only for the $10^0$ or $10^{-1}$ dilution plates. The microbial reduction is then calculated at the specified time points.

In order to demonstrate the suitability of the medium used for growth of the test organisms and to provide an estimation of the initial inoculum concentration, inoculum controls are prepared by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0 \times 10^5$ and $1.0 \times 10^6$ cfu/mL.

The data for *Pseudomonas aeruginosa, Serratia marcescens* is not reported in Table 2 as complete kill was observed and recorded across all of the solutions.

TABLE 2

| Biocidal data at 4 and 24 hours. | | | | | | |
|---|---|---|---|---|---|---|
| | CE3 | CE4 | 2 | 3 | 4 | CE 5 |
| Biocidal (4 hours) | | | | | | |
| S. aureus | 3.1 | 3.6 | >4.7 | >4.7 | 4.7 | 3.9 |
| C. albicans | 3.4 | 3.4 | >4.6 | >4.6 | 4.6 | 3.3 |
| F. solani | 3.3 | 3.3 | 3.7 | 4.2 | 4.2 | 4.0 |
| Biocidal (24 hours) | | | | | | |
| C. albicans | 4.1 | 3.3 | >4.6 | >4.6 | >4.6 | 3.8 |
| F. solani | 3.6 | 3.4 | 3.8 | 3.9 | >4.2 | 3.9 |
| peroxide residual (ppm) | nd | 40 | nd | nd | 95 | nd |

Figure 7:
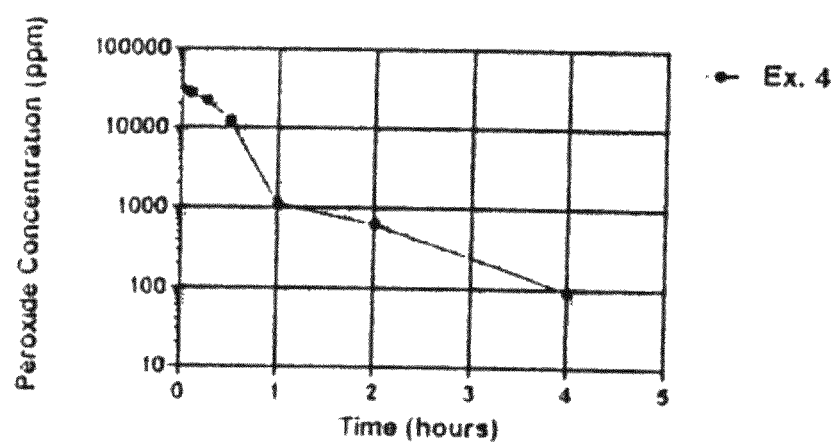
FIG. 7 is a plot of a neutralization rate profile of a peroxide disinfection solution of the invention against Clear Care® in identically manufactured lens cases.

FIG. 7 is a peroxide neutralization plot for two solutions: Comparative Ex. No. 5 and Example No. 2. As indicated by the plot data, the presence of the amino buffer component, TRIS, in the peroxide disinfection solution of Example No. 2 shows a significant reduction in the rate of peroxide neutralization over the initial four hours. A calculation that measures the area under the neutralization curves indicate that the total peroxide concentration in the TRIS buffered peroxide solution of Example No. 2 over the first four hours is about 67% greater than the phosphate buffered peroxide solution of CE5.

Figure 8:
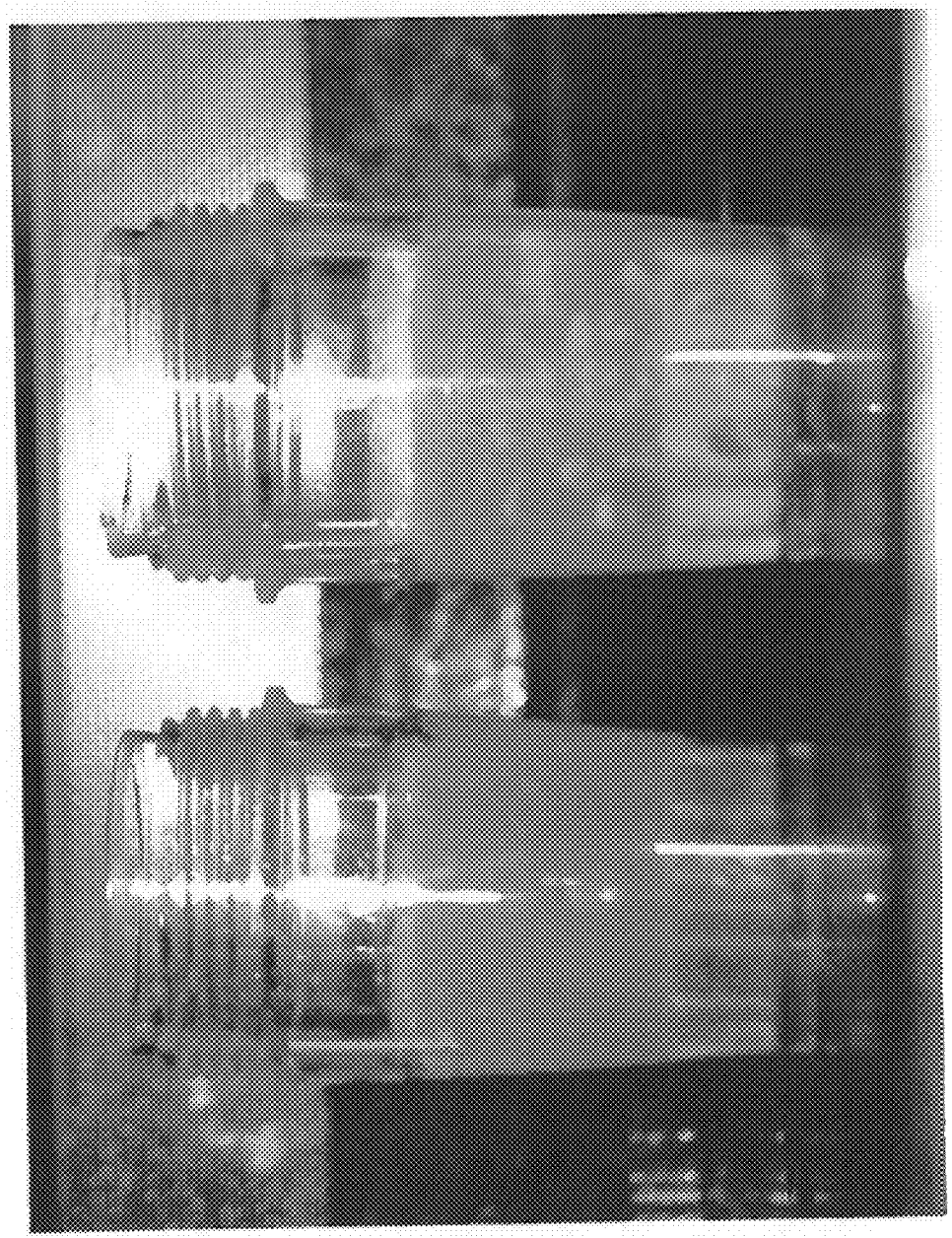
FIG. 8 is a photograph showing a visual comparison of a peroxide, contact lens care solution containing TRIS vs. Clear Care® in contact lens closures provided with an EZ-Sept® peroxide disinfection system.

FIG. 8 is a peroxide neutralization plot of Example No. 4. As indicated by the plot data, the presence of the amino buffer component, TRIS in the presence of taurine shows a very similar peroxide neutralization as Example No. 2 over the initial four hours.

FIG. 9 is a photograph showing a visual comparison of a contact lens care solution of Example 2 (on the left) vs. the solution provided with the Clear Care® peroxide system by CibaVision (on the right) in contact lens closures provided with EZ-Sept® peroxide system available from Bausch+ Lomb, Rochester, N.Y. The solutions were simultaneously added to the respective lens cclosures equipped with a peroxide neutralization catalyst comprising platinum attached to the bottom of the closures. The photograph was taken within one minute following introduction of each respective solution into the lens closure. With the photograph one can visualize the affect TRIS has on modulating the peroxide neutralizing activity of the catalyst. The Clear Care® peroxide disinfection solution reacts almost violently upon contact with the neutralization catalyst within the first minute generating large non-uniform bubbles of dioxygen (a neutralization product of hydrogen peroxide). Visual examination of the catalyst surface shows a relatively fast neutralization reaction as evident by the extensive generation of smaller bubbles at the catalyst surface, which then coalesce to form the larger bubbles that percolate up through the solution. One can also visualize a relatively large foam head generated at the top of the solution, again indicating a relatively high rate of peroxide neutralization in the first minute of neutralization.

Figure 6:
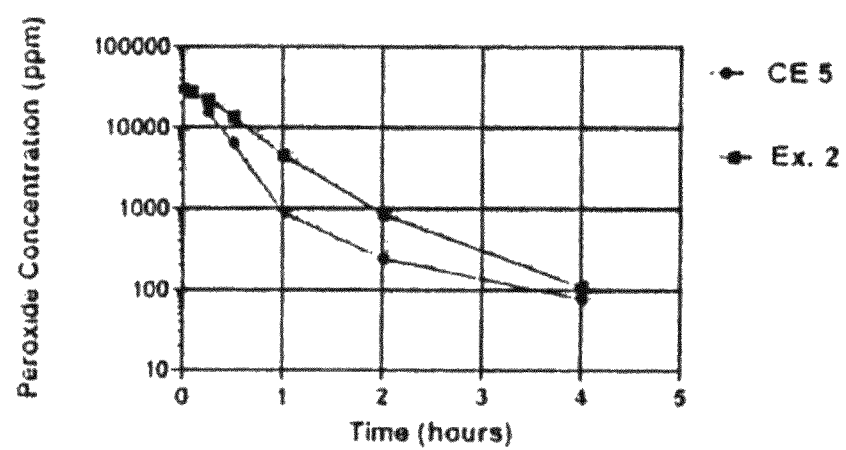
FIG. 6 is a comparative plot of neutralization rate profiles of a peroxide disinfection solution of the invention against a similar peroxide solution but with a phosphate buffer.

In contrast, with the peroxide disinfection solution of Example 2 one witnesses a more controlled, significantly slower rate of peroxide neutralization within the first minute of contact. Instead of a violent neutralization reaction one observes a relatively constant fizz, or a generation of substantially uniform microbubbles that slowly percolate up through the solution. In fact, by looking at the surface of the catalyst one can actually visualize a much slower rate of peroxide neutralization compared to the Clear Care® peroxide solution as well as a relatively small foam head. The visualization of the peroxide neutralization rate during the first minute is consistent with what one observes with the calculated (titrated) neutralization profiles plotted in FIGS. 5 to 7. More portantly, the visualized rate of peroxide neutralization is consistent with the observed increase in biocidal efficacy of the inventive lens care systems, particularly, against *Candida albicans*, typically, the most difficult of the five microorganisms to kill.

EXAMPLES 5 to 11

The following peroxide contact lens care solutions are prepared by adding the appropriate amounts of each of the listed components to purified water. The amounts of sodium phosphate, citric acid, potassium chloride, poloxamer L81 and hydrogen peroxide in each Example formulation are as reported in Comparative Example 5, Table 1.

TABLE 3

| | Example No. | | | | | | |
|---|---|---|---|---|---|---|---|
| | 5 | 6 | 7 | 8 | 9 | 10 | 11 |
| glutamine | 0.2 | — | — | — | — | — | — |
| asparagine | — | 0.2 | — | — | — | — | — |
| lysine | — | — | 0.2 | — | — | — | — |
| glycine | — | — | — | 0.2 | — | — | — |
| serine | — | — | — | — | 0.2 | — | — |
| glycylserine | — | — | — | — | — | 0.2 | — |
| diglycine | — | — | — | — | — | — | 0.2 |

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention.

I claim:

1. A contact lens disinfection system comprising:
a peroxide disinfection solution comprising 0.5 wt. % to 6 wt. % hydrogen peroxide or a chemical precursor of hydrogen peroxide, and an amino buffer component at a concentration from 0.04 wt. % to 0.3 wt. %, wherein the amino buffer component is 2-amino-2-hydroxymethyl-1,3-propane diol;
in combination with a lens closure comprising securing elements to position and maintain a pair of contact lenses in the disinfection solution, and a peroxide neutralization catalyst comprising platinum,
wherein the amino buffer component is present at an effective concentration such that the disinfection system exhibits a pseudo first-order, half-life of hydrogen peroxide over an initial sixty minutes of neutralization from 12 minutes to 30 minutes in the lens closure.

2. A contact lens disinfection system comprising:
a peroxide disinfection solution comprising 0.5 wt. % to 6 wt. % hydrogen peroxide or a chemical precursor of hydrogen peroxide, and an amino buffer component at a concentration from 0.04 wt. % to 0.3 wt. %, wherein the amino buffer component is 2-amino-2-hydroxymethyl-1,3-propane diol;
in combination with a lens closure comprising securing elements to position and maintain a pair of contact lenses in the disinfection solution, and a peroxide neutralization catalyst comprising platinum;
wherein the amino buffer component is present at an effective concentration such that the disinfection system exhibits greater biocidal efficacy against Candida albicans or Serratia marcescens by 0.5 log-kill or greater after six hours than an equivalent contact lens disinfection solution in the absence of the amino buffer component, wherein the increase in effectiveness against Candida albicans or Serratia marcescens is provided by a delay in peroxide neutralization of the solution.

3. The lens disinfection system of claim 1 wherein the pseudo first-order, half-life of hydrogen peroxide over the initial sixty minutes is from 14 minutes to 22 minutes, and the concentration of hydrogen peroxide after an initial six hours of neutralization is less than 150 ppm.

4. The lens disinfection system of claim 1 wherein the disinfection solution further comprises an amino acid or a compound derived from an amino acid.

5. The lens disinfection system of claim 4 wherein the amino acid is selected from the group consisting of methionine, aspargine, glutamine, histidine, lysine, arginine, glycine, serine, cystine and threonine.

6. The lens disinfection system of claim 4 wherein the amino acid is present in the disinfection solution from 0.05 wt. % to 0.4 wt. %.

7. The lens disinfection system of claim 1 wherein the disinfection solution further comprises a low foam surfactant, particularly a polyoxyethylene-polyoxypropylene condensation polymer selected from the group consisting of Pluronic® L42, Pluronic® L43, Pluronic® L61, Pluronic® L81, Pluronic® 31R1, Pluronic® 31R2, Pluronic® 25R1, Pluronic® 17R1, Pluronic® 17R2, Pluronic® 12R3 and Pluronic® 17R4.

8. The lens disinfection system of claim 1 wherein the disinfection system exhibits a hydrogen peroxide neutralization profile that is more effective against Candida albicans by 0.8 log-kill or greater after six hours than an equivalent contact lens disinfection solution in the absence of the amino buffer component.

9. A contact lens disinfection system comprising:
a peroxide disinfection solution comprising 0.5 wt. % to 6 wt. % hydrogen peroxide or a chemical precursor of hydrogen peroxide, and an amino buffer component, wherein the amino buffer component is 2-amino-2-hydroxymethyl-1,3-propane diol;
in combination with a lens closure comprising securing elements to position and maintain a pair of contact lenses in the disinfection solution, and a peroxide neutralization catalyst comprising platinum,
wherein the amino buffer component is present at a concentration of from 0.01 wt. % to 0.3 wt. % and the disinfection system exhibits a pseudo first-order, half-life of hydrogen peroxide over an initial sixty minutes of neutralization from 12 minutes to 30 minutes in the lens closure.

10. The lens disinfection system of claim 9 wherein the pseudo first-order, half-life of hydrogen peroxide over the initial sixty minutes is from 14 minutes to 22 minutes, and the concentration of hydrogen peroxide after an initial six hours of neutralization is less than 150 ppm.

11. The lens disinfection system of claim 9 wherein the disinfection system exhibits greater biocidal efficacy against Candida albicans or Serratia marcescens by 0.5 log-kill or greater after six hours than an equivalent contact lens disinfection solution in the absence of the amino buffer component, wherein the increase in effectiveness against Candida albicans or Serratia marcescens is provided by a delay in peroxide neutralization of the solution.

12. The disinfection system of claim 11 wherein the disinfection system exhibits a hydrogen peroxide neutralization profile that is more effective against Candida albicans by 0.8 log-kill or greater after six hours than the equivalent contact lens disinfection solution.

13. The lens disinfection system of claim 9 wherein the disinfection solution further comprises an amino acid or a compound derived from an amino acid.

14. The disinfection system of claim 9 wherein the molar ratio of hydrogen peroxide to the amino buffer component is from 10:1 to 200:1.

* * * * *